(12) United States Patent
Miyachi

(10) Patent No.: US 12,357,276 B2
(45) Date of Patent: Jul. 15, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 18/296,038

(22) Filed: Apr. 5, 2023

(65) Prior Publication Data

US 2023/0233186 A1    Jul. 27, 2023

Related U.S. Application Data

(63) Continuation of application No. PCT/JP2021/036816, filed on Oct. 5, 2021.

(30) Foreign Application Priority Data

Oct. 16, 2020  (JP) ................. 2020-174675

(51) Int. Cl.
*A61B 8/00* (2006.01)
*A61B 8/08* (2006.01)

(52) U.S. Cl.
CPC ............... *A61B 8/463* (2013.01); *A61B 8/08* (2013.01); *A61B 8/465* (2013.01); *A61B 8/467* (2013.01); *A61B 8/5223* (2013.01)

(58) Field of Classification Search
CPC ........... A61B 8/463; A61B 8/08; A61B 8/465; A61B 8/467; A61B 8/5223
See application file for complete search history.

(56) References Cited

U.S. PATENT DOCUMENTS

2011/0137169 A1    6/2011  Akaki et al.
2018/0166167 A1*   6/2018  Kanada ................. G06T 7/0012
(Continued)

FOREIGN PATENT DOCUMENTS

| JP | 2011-139896 A | 7/2011 |
|----|---------------|--------|
| JP | 2014-039852 A | 3/2014 |
| JP | 2018-097463 A | 6/2018 |

OTHER PUBLICATIONS

International Search Report issued in PCT/JP2021/036816; mailed Dec. 21, 2021.
(Continued)

*Primary Examiner* — Alexei Bykhovski
(74) *Attorney, Agent, or Firm* — Studebaker Brackett PLLC

(57) ABSTRACT

An ultrasound diagnostic apparatus (1) includes an ultrasound probe (2) and a diagnostic apparatus body (3) connected to the ultrasound probe (2), in which the diagnostic apparatus body (3) includes a monitor (15) on which an ultrasound diagnosis image and a plurality of diagnostic finding icons corresponding to a plurality of determined diagnostic findings are displayed, a similarity determination unit (18) that determines similarity between the ultrasound diagnosis image and each of a plurality of image patterns corresponding to the plurality of diagnostic findings, and a display position changing unit (19) that changes display positions of the plurality of diagnostic finding icons on the monitor in accordance with the similarity determined by the similarity determination unit (18).

12 Claims, 12 Drawing Sheets

(56) References Cited

U.S. PATENT DOCUMENTS

| | | | |
|---|---|---|---|
| 2019/0038261 A1* | 2/2019 | Ebata | A61B 8/469 |
| 2019/0239860 A1* | 8/2019 | Hayashi | A61B 8/463 |
| 2019/0307429 A1* | 10/2019 | Matsumoto | A61B 8/5223 |
| 2022/0061813 A1* | 3/2022 | Halmann | A61B 5/08 |

OTHER PUBLICATIONS

International Preliminary Report on Patentability (Chapter I) and Written Opinion of the International Searching Authority issued in PCT/JP2021/036816; issued Apr. 13, 2023.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2021/036816 filed on Oct. 5, 2021, which claims priority under 35 U.S.C. § 119(a) to Japanese Patent Application No. 2020-174675 filed on Oct. 16, 2020. The above applications are hereby expressly incorporated by reference, in their entirety, into the present application.

BACKGROUND OF THE INVENTION

1. Field of the Invention

The present invention relates to an ultrasound diagnostic apparatus that supports diagnosis using an ultrasound image, and a control method of an ultrasound diagnostic apparatus.

2. Description of the Related Art

In the related art, ultrasound images of each part of a subject have been captured using an ultrasound diagnostic apparatus, and diagnosis of the parts imaged in the ultrasound images has been performed using the obtained ultrasound images. For example, the information processing apparatus disclosed in JP2014-039852A has been developed so that a user can easily perform diagnosis using the ultrasound images. The information processing apparatus in JP2014-039852A stores ultrasound images of a plurality of frames captured in the past, searches for an ultrasound image representing a medical case similar to a medical case of a part of a subject as a target to be diagnosed from the ultrasound images of the plurality of frames, and displays the ultrasound image.

SUMMARY OF THE INVENTION

However, even in a case of using the information processing apparatus in JP2014-039852A to refer to the ultrasound image representing a similar medical case to the part of the subject as a target to be diagnosed, it may be difficult for a user not familiar with diagnosis of the subject using ultrasound images to determine which diagnostic finding is to be assigned to the ultrasound image in which the part of the target to be diagnosed is imaged.

An object of the present invention is to provide an ultrasound diagnostic apparatus with which a user can easily assign a diagnostic finding to an ultrasound image, and a control method of an ultrasound diagnostic apparatus.

An ultrasound diagnostic apparatus according to an aspect of the present invention comprises an ultrasound probe, and a diagnostic apparatus body connected to the ultrasound probe, in which the diagnostic apparatus body includes a monitor on which an ultrasound diagnosis image and a plurality of diagnostic finding icons corresponding to a plurality of determined diagnostic findings are displayed, a similarity determination unit that determines similarity between the ultrasound diagnosis image and each of a plurality of image patterns corresponding to the plurality of diagnostic findings, and a display position changing unit that changes display positions of the plurality of diagnostic finding icons on the monitor in accordance with the similarity determined by the similarity determination unit.

It is preferable that the diagnostic apparatus body includes an input device for a user to perform an input operation, and a diagnostic finding linking unit that links the diagnostic finding corresponding to the diagnostic finding icon selected through the input device among the plurality of diagnostic finding icons displayed on the monitor to the ultrasound diagnosis image.

It is preferable that the diagnostic finding linked to the ultrasound diagnosis image by the diagnostic finding linking unit is displayed on the monitor.

The display position changing unit may arrange the plurality of diagnostic finding icons corresponding to the plurality of diagnostic findings in a descending order of the similarity.

In this case, the display position changing unit may display a diagnostic finding icon corresponding to a diagnostic finding of highest similarity among the plurality of diagnostic findings to be larger than the other diagnostic finding icons.

It is preferable that the ultrasound diagnosis image is an ultrasound image obtained by imaging a lung of a subject, and at least one of the plurality of diagnostic findings includes a diagnostic finding of any of B-line, consolidation, normality, and absence of lung sliding.

The ultrasound diagnosis image may be a still image at a time of freezing, and the still image may be displayed on the monitor.

In addition, the ultrasound diagnosis image may be a video image. In this case, it is preferable that the ultrasound diagnosis image is a video image in a determined time until freezing.

In addition, the similarity determination unit may determine similarity between ultrasound images of a plurality of frames constituting the video image and each of the plurality of image patterns corresponding to the plurality of diagnostic findings, an ultrasound image of highest similarity among the ultrasound images of the plurality of frames may be displayed on the monitor, and the display position changing unit may change the display positions of the plurality of diagnostic finding icons based on the ultrasound image of the highest similarity.

A control method of an ultrasound diagnostic apparatus according to another aspect of the present invention comprises displaying an ultrasound diagnosis image and a plurality of diagnostic finding icons corresponding to a plurality of determined diagnostic findings on a monitor, determining similarity between the ultrasound diagnosis image and each of a plurality of image patterns corresponding to the plurality of diagnostic findings, and changing display positions of the plurality of diagnostic finding icons on the monitor in accordance with the determined similarity.

According to the present invention, an ultrasound diagnostic apparatus comprises an ultrasound probe, and a diagnostic apparatus body connected to the ultrasound probe, in which the diagnostic apparatus body includes a monitor on which an ultrasound diagnosis image and a plurality of diagnostic finding icons corresponding to a plurality of determined diagnostic findings are displayed, a similarity determination unit that determines similarity between the ultrasound diagnosis image and each of a plurality of image patterns corresponding to the plurality of diagnostic findings, and a display position changing unit that changes display positions of the plurality of diagnostic finding icons on the monitor in accordance with the similarity determined by the similarity determination unit. Thus, a user can easily assign a diagnostic finding to an ultrasound image.

DESCRIPTION OF THE PREFERRED EMBODIMENTS

Hereinafter, embodiments of the invention will be described with reference to the accompanying drawings.

The description of configuration requirements described below is provided based on the representative embodiment of the present invention, but the present invention is not limited to such an embodiment.

In the present specification, a numerical range represented using "to" means a range including the numerical values before and after "to" as a lower limit value and an upper limit value.

In the present specification, the terms "identical" and "same" include an error range generally allowed in the technical field.

Embodiment 1

Figure 1:
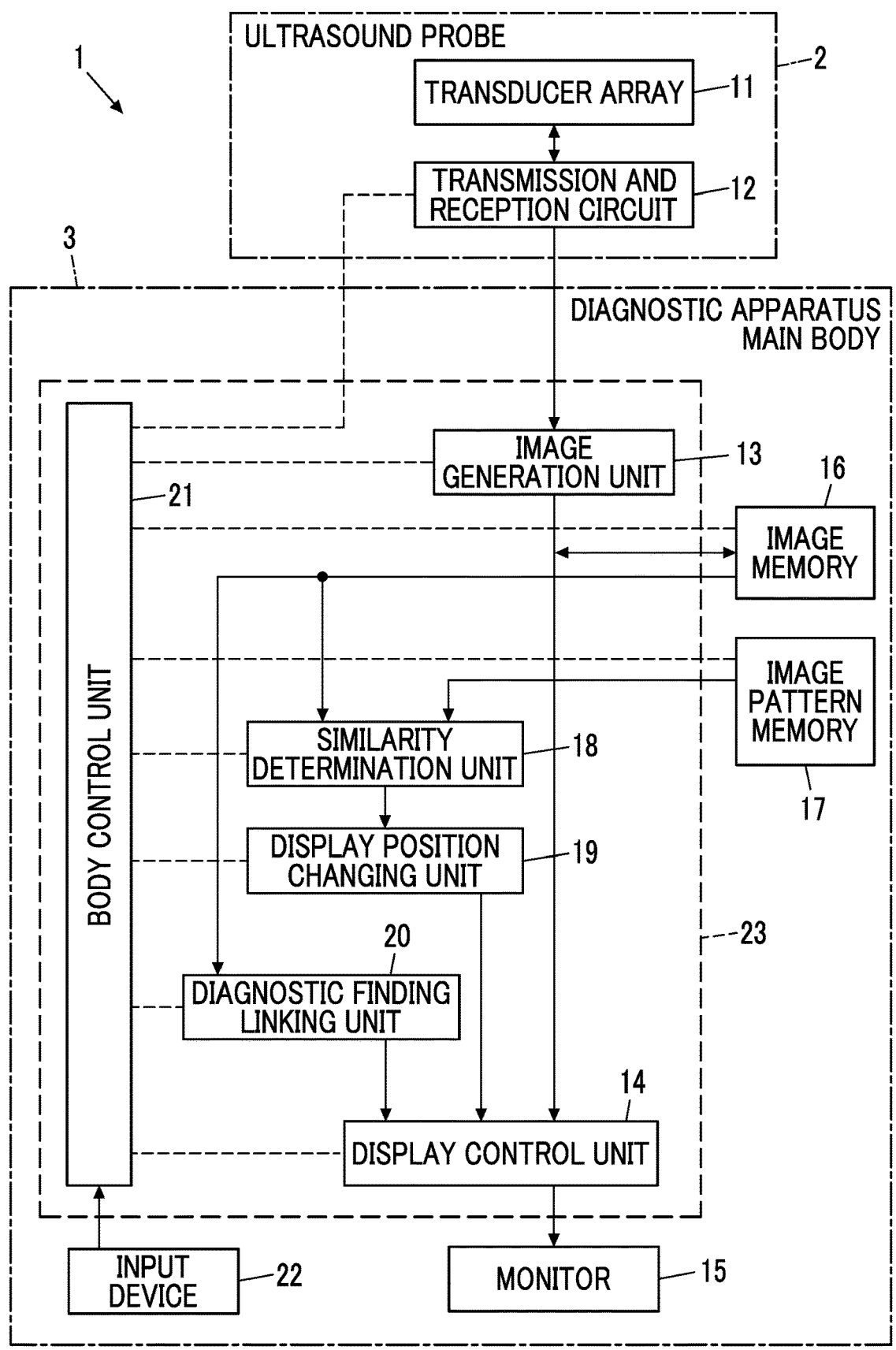
FIG. 1 is a block diagram illustrating a configuration of an ultrasound diagnostic apparatus according to Embodiment 1 of the present invention.

FIG. 1 illustrates a configuration of an ultrasound diagnostic apparatus 1 according to Embodiment 1 of the present invention. The ultrasound diagnostic apparatus 1 comprises an ultrasound probe 2 and a diagnostic apparatus body 3.

The ultrasound probe 2 comprises a transducer array 11. A transmission and reception circuit 12 is connected to the transducer array 11.

The diagnostic apparatus body 3 comprises an image generation unit 13. The image generation unit 13 is connected to the transmission and reception circuit 12 of the ultrasound probe 2. In addition, a display control unit 14 and a monitor 15 are sequentially connected to the image generation unit 13. In addition, an image memory 16 is connected to the image generation unit 13. In addition, the diagnostic apparatus body 3 comprises an image pattern memory 17. A similarity determination unit 18 is connected to the image memory 16 and to the image pattern memory 17. A display position changing unit 19 is connected to the similarity determination unit 18. The display position changing unit 19 is connected to the display control unit 14. In addition, a diagnostic finding linking unit 20 is connected to the image memory 16. The diagnostic finding linking unit 20 is connected to the display control unit 14.

In addition, a body control unit 21 is connected to the transmission and reception circuit 12 of the ultrasound probe 2, the image generation unit 13, the display control unit 14, the image memory 16, the image pattern memory 17, the similarity determination unit 18, the display position changing unit 19, and the diagnostic finding linking unit 20. In addition, an input device 22 is connected to the body control unit 21.

In addition, a processor 23 is composed of the image generation unit 13, the display control unit 14, the similarity determination unit 18, the display position changing unit 19, the diagnostic finding linking unit 20, and the body control unit 21.

The transducer array 11 of the ultrasound probe 2 illustrated in FIG. 1 includes a plurality of ultrasound oscillators that are one-dimensionally or two-dimensionally arranged. Each of these ultrasound oscillators transmits an ultrasound wave in accordance with a drive signal supplied from the transmission and reception circuit 12, and receives an ultrasound echo from a subject and outputs a signal based on the ultrasound echo. Each ultrasound oscillator is configured by forming an electrode at both ends of a piezoelectric body consisting of, for example, a piezoelectric ceramic represented by lead zirconate titanate (PZT), a polymer piezoelectric element represented by polyvinylidene difluoride (PVDF), and a piezoelectric single crystal represented by a lead magnesium niobate-lead titanate (PMN-PT).

Figure 2:
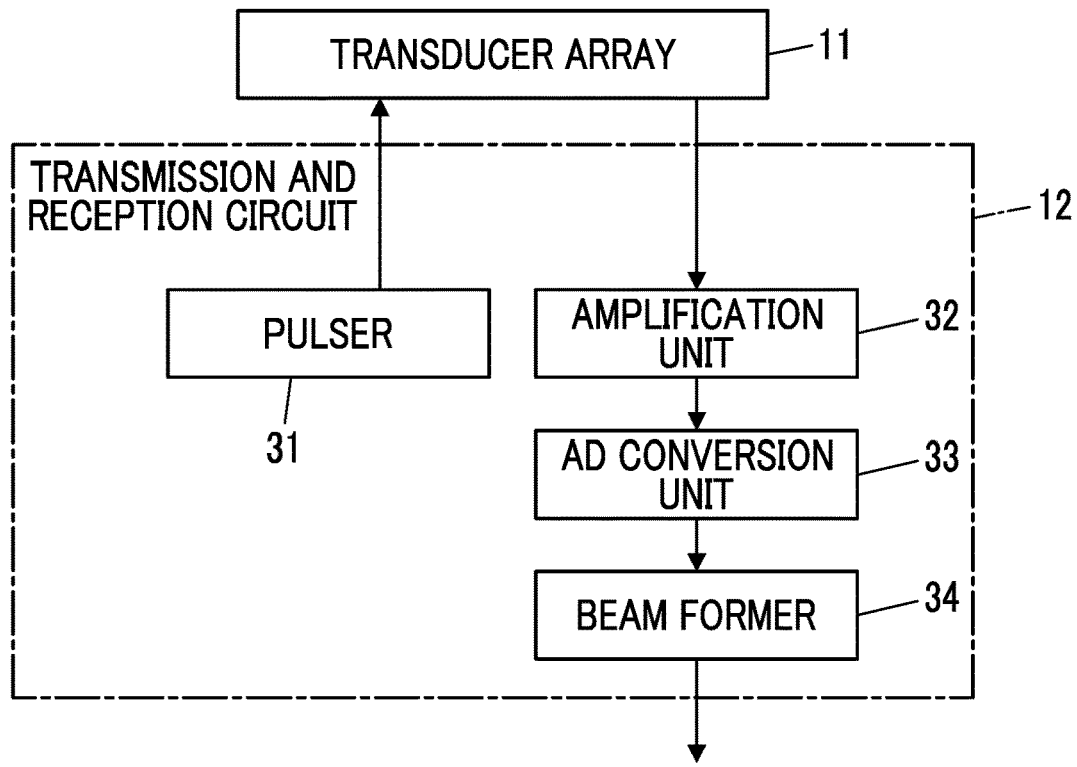
FIG. 2 is a block diagram illustrating a configuration of a transmission and reception circuit in Embodiment 1 of the present invention.

The transmission and reception circuit 12, under control of the body control unit 21, transmits the ultrasound wave from the transducer array 11 and generates a sound ray signal based on a reception signal acquired by the transducer array 11. As illustrated in FIG. 2, the transmission and reception circuit 12 includes a pulser 31 connected to the transducer array 11 and an amplification unit 32, an analog digital (AD) conversion unit 33, and a beam former 34 that are sequentially connected in series from the transducer array 11.

The pulser 31 includes, for example, a plurality of pulse generators and supplies each drive signal to the plurality of ultrasound oscillators by adjusting a delay amount of each drive signal based on a transmission delay pattern selected in accordance with a control signal from the body control unit 21 so that the ultrasound waves transmitted from the plurality of ultrasound oscillators of the transducer array 11 form an ultrasound beam. In a case where a voltage having a pulse shape or a continuous wave shape is applied to the electrodes of the ultrasound oscillators of the transducer array 11, the piezoelectric body expands and contracts to generate an ultrasound wave having a pulse shape or a continuous wave shape from each ultrasound oscillator, and an ultrasound beam is formed from a combined wave of the ultrasound waves.

The transmitted ultrasound beam is reflected by, for example, a target such as a part of the subject and propagates toward the transducer array 11 of the ultrasound probe 2. The ultrasound echo propagating toward the transducer array 11 is received by each ultrasound oscillator constituting the transducer array 11. At this point, each ultrasound oscillator constituting the transducer array 11, by receiving the propagating ultrasound echo, expands and contracts to generate the reception signal that is an electric signal and outputs the reception signal to the amplification unit 32.

The amplification unit 32 amplifies the signal input from each ultrasound oscillator constituting the transducer array 11 and transmits the amplified signal to the AD conversion unit 33. The AD conversion unit 33 converts the signal transmitted from the amplification unit 32 into digital reception data. The beam former 34 performs so-called reception focus processing by applying a delay to each reception data received from the AD conversion unit 33 and by adding each reception data. Through the reception focus processing, the sound ray signal in which each reception data converted by the AD conversion unit 33 is phased and added, and in which a focus of the ultrasound echo is narrowed is acquired.

Figure 3:
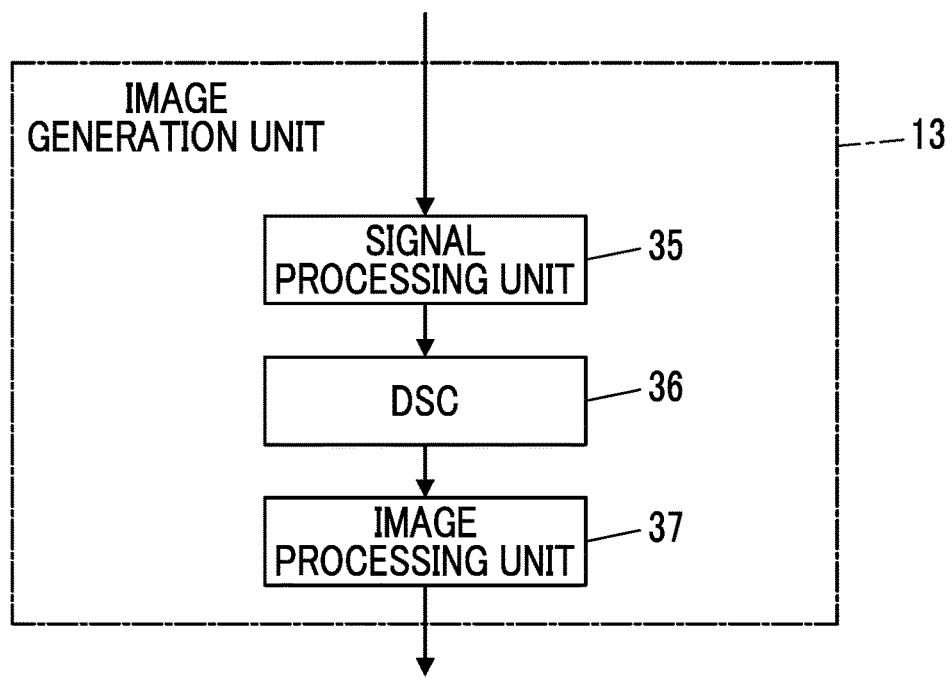
FIG. 3 is a block diagram illustrating a configuration of an ultrasound image generation unit in Embodiment 1 of the present invention.

The image generation unit 13 has a configuration in which a signal processing unit 35, a digital scan converter (DSC) 36, and an image processing unit 37 are sequentially connected in series as illustrated in FIG. 3.

The signal processing unit 35 corrects attenuation by distance in accordance with depths of reflection positions of the ultrasound waves using a sound speed value set by the body control unit 21 and then, performs envelope detection processing with respect to the sound ray signal received from the transmission and reception circuit 12, thereby generating a B-mode image signal that is tomographic image information related to tissues inside the subject.

The DSC 36 converts the B-mode image signal generated by the signal processing unit 35 into an image signal complying with a scanning method of a typical television signal (raster conversion).

The image processing unit 37 performs various types of necessary image processing such as gradation processing on the B-mode image signal input from the DSC 36 and then, transmits the B-mode image signal to the display control unit 14 and to the image memory 16. Hereinafter, the B-mode image signal on which the image processing is performed by the image processing unit 37 will be referred to as an ultrasound image.

The image memory 16 stores the ultrasound image generated by the image generation unit 13. The ultrasound image stored in the image memory 16 is read out under control of the body control unit 21 and is transmitted to the display control unit 14, the similarity determination unit 18, and the diagnostic finding linking unit 20.

For example, recording media such as a flash memory, a hard disk drive (HDD), a solid state drive (SSD), a flexible disk (FD), a magneto-optical disc (MO disc), a magnetic tape (MT), a random access memory (RAM), a compact disc (CD), a digital versatile disc (DVD), a secure digital card (SD card), and a universal serial bus memory (USB memory) can be used as the image memory 16.

The image pattern memory 17 stores a plurality of image patterns corresponding to a plurality of diagnostic findings determined for parts of the subject. For example, diagnostic findings of so-called B-line, consolidation, normality, and absence of lung sliding are known as a diagnostic finding for a lung of the subject. Characteristic image patterns appearing in the ultrasound image in accordance with these diagnostic findings are also known. For example, the image patterns corresponding to the diagnostic findings can be stored in advance in the image pattern memory 17 by a user.

In addition, like the image memory 16, for example, recording media such as a flash memory, a HDD, a SSD, a FD, a MO disc, a MT, a RAM, a CD, a DVD, a SD card, and a USB memory can be used as the image pattern memory 17.

The similarity determination unit 18 determines similarity between an ultrasound diagnosis image generated by the image generation unit 13 and stored in the image memory 16 and each of the plurality of image patterns stored in the image pattern memory 17. For example, in a case where image patterns corresponding to four diagnostic findings of B-line, consolidation, normality, and absence of lung sliding are stored in the image pattern memory 17, the similarity determination unit 18 determines similarity between each of the four image patterns and the ultrasound diagnosis image and obtains four values of similarity.

Here, the ultrasound diagnosis image includes a still image consisting of the ultrasound image of one frame and a video image consisting of the ultrasound images of a plurality of frames generated by the image generation unit 13.

As a method of determining the similarity, for example, the similarity determination unit 18 can use a method using simple template matching, a machine learning technique disclosed in Csurka et al.: Visual Categorization with Bags of Keypoints, Proc. of ECCV Workshop on Statistical Learning in Computer Vision, pp. 59-74 (2004), or a general image recognition technique using deep learning disclosed in Krizhevsk et al.: ImageNet Classification with Deep Convolutional Neural Networks, Advances in Neural Information Processing Systems 25, pp. 1106-1114 (2012).

The display position changing unit 19 stores a plurality of diagnostic finding icons corresponding to the plurality of diagnostic findings for the part of the subject together with display positions determined on the monitor 15, and changes display positions of the plurality of diagnostic finding icons in accordance with the similarity corresponding to each of the plurality of diagnostic findings determined by the similarity determination unit 18. Here, each of diagnostic finding icons J1 to J4 has a design resembling an image pattern of a corresponding diagnostic finding so that the user can easily recognize the diagnostic finding icons J1 to J4 and the diagnostic findings in association with each other.

In addition, for example, the display position changing unit 19 can change the display positions of the plurality of diagnostic finding icons such that the plurality of diagnostic finding icons corresponding to the plurality of diagnostic findings are arranged in a descending order of the similarity.

Figure 4:
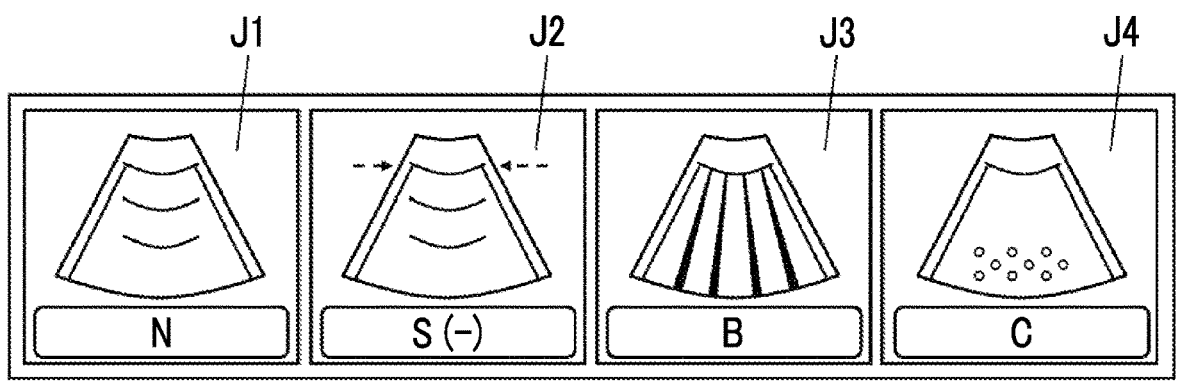
FIG. 4 is a diagram illustrating an example of a plurality of diagnostic finding icons arranged in a predetermined order in Embodiment 1 of the present invention.
Figure 5:
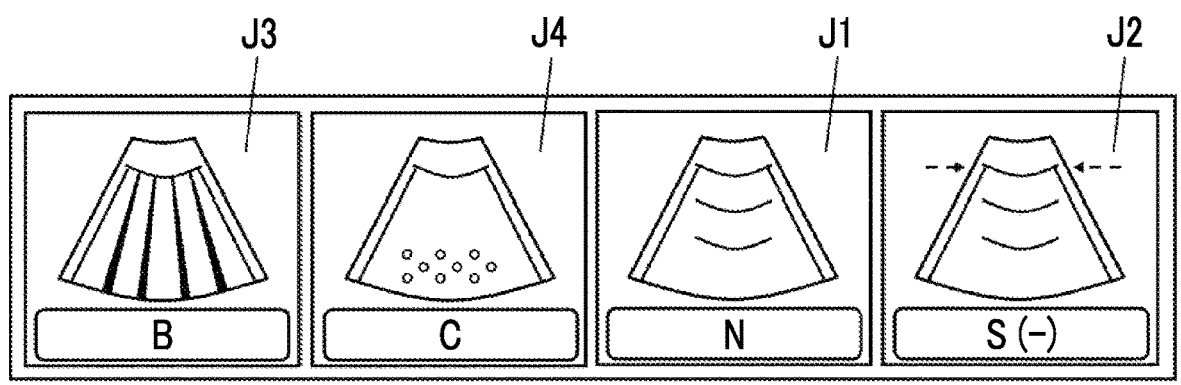
FIG. 5 is a diagram illustrating an example of the plurality of diagnostic finding icons after the order is changed in Embodiment 1 of the present invention.

For example, as illustrated in FIG. 4, it is assumed that the display position changing unit 19 stores the four diagnostic finding icons J1 to J4 of normality (N), absence of lung sliding (S(-)), B-line (B), and consolidation (C) for the lung of the subject together with display positions at which the diagnostic finding icons J1, J2, J3, and J4 are arranged in this order from the left. For example, in a case where the similarity is determined by the similarity determination unit 18 such that values are decreased in order of B-line, consolidation, normality, and absence of lung sliding, the display position changing unit 19 can change the display positions of the four diagnostic finding icons J1 to J4 such that the diagnostic finding icons J3, J4, J1, and J2 are arranged in this order from the left as illustrated in FIG. 5.

The plurality of diagnostic finding icons J1 to J4 of which the display positions are changed in such a manner are transmitted to the display control unit 14 and are displayed on the monitor 15.

Here, the diagnostic finding of normality refers to a finding indicating that a boundary of a pleura and an artifact (a so-called A-line) that is caused by multiple reflection of the ultrasound waves and that extends along a direction orthogonal to a depth direction are included in the ultrasound image, and that the boundary of the pleura captured in the ultrasound image is displaced to a certain degree or higher in the continuous ultrasound images of the plurality of frames (so-called lung sliding is recognized). Accordingly, the finding of normality is a finding indicating that A-line is included in the ultrasound image, and that lung sliding is recognized. The finding of absence of lung sliding refers to a finding indicating that in the ultrasound image, the boundary of the pleura and the artifact (A-line) that is caused by multiple reflection and that extends along the direction orthogonal to the depth direction are included, and that the boundary of the pleura captured in the ultrasound image is almost not displaced in the continuous ultrasound images of the plurality of frames because of so-called pneumothorax or the like (lung sliding is not recognized). Accordingly, the finding of absence of lung sliding is a finding indicating that while A line is included in the ultrasound image as in the finding of normality, lung sliding is not recognized. Generally, the finding of absence of lung sliding is known to indicate that so-called pneumothorax is suspected. The diagnostic finding of B-line refers to a finding indicating that a linear pattern along the depth direction is included in the ultrasound image because of pleural edema or the like. In addition, the finding of consolidation refers to a finding indicating that a granular pattern is included in the ultrasound image because of pulmonary edema or the like.

The body control unit 21 controls each part of the ultrasound probe 2 and each part of the diagnostic apparatus body 3 in accordance with a program and the like recorded in advance.

The display control unit 14, under control of the body control unit 21, performs predetermined processing on the ultrasound image generated by the image generation unit 13, the plurality of diagnostic finding icons J1 to J4 of which the display positions are changed by the display position changing unit 19, and the like and displays the ultrasound image, the plurality of diagnostic finding icons J1 to J4, and the like on the monitor 15.

The monitor 15 performs various types of display under control of the display control unit 14. Examples of the monitor 15 include display devices such as a liquid crystal display (LCD) and an organic electroluminescence display (organic EL display).

The input device 22 is used for the user to perform an input operation. For example, the input device 22 is composed of a device such as a keyboard, a mouse, a trackball, a touchpad, and a touch panel for the user to perform the input operation.

The diagnostic finding linking unit 20 links, to the ultrasound image, a diagnostic finding corresponding to a diagnostic finding icon selected by the user through the input device 22 among the diagnostic finding icons J1 to J4 displayed on the monitor 15. For example, as illustrated in FIG. 5, in a case where the four diagnostic finding icons J1 to J4 are displayed on the monitor 15, and the diagnostic finding icon J3 corresponding to the diagnostic finding of B-line of which the similarity is the highest is selected by the user through the input device 22, the ultrasound image used for determination of the similarity by the similarity determination unit 18 is linked to the diagnostic finding of B-line corresponding to the diagnostic finding icon J3 selected by the user.

The processor 23 including the image generation unit 13, the display control unit 14, the similarity determination unit 18, the display position changing unit 19, the diagnostic finding linking unit 20, and the body control unit 21 is composed of a central processing unit (CPU) and a control program causing the CPU to perform various types of processing, but may also be configured using a field programmable gate array (FPGA), a digital signal processor (DSP), an application specific integrated circuit (ASIC), a graphics processing unit (GPU), or other integrated circuits (IC) or may also be composed of a combination thereof.

In addition, a part or all of the image generation unit 13, the display control unit 14, the similarity determination unit 18, the display position changing unit 19, the diagnostic finding linking unit 20, and the body control unit 21 can be configured to be integrated into one CPU or the like.

Next, an operation of the ultrasound diagnostic apparatus 1 according to Embodiment 1 of the present invention will be described using the flowchart illustrated in FIG. 6. While an example of examining the lung of the subject will be described in the following operation description, an examination part of the subject is not limited to the lung.

In addition, in the following operation description, the ultrasound diagnostic apparatus 1 comprises a touch sensor disposed to be overlaid on the monitor 15 as the input device 22.

In addition, the image pattern memory 17 stores a plurality of image patterns corresponding to a plurality of diagnostic findings of the lung of the subject. In addition, the display position changing unit 19 stores the plurality of diagnostic finding icons J1 to J4 corresponding to the plurality of diagnostic findings of the lung of the subject.

Figure 7:
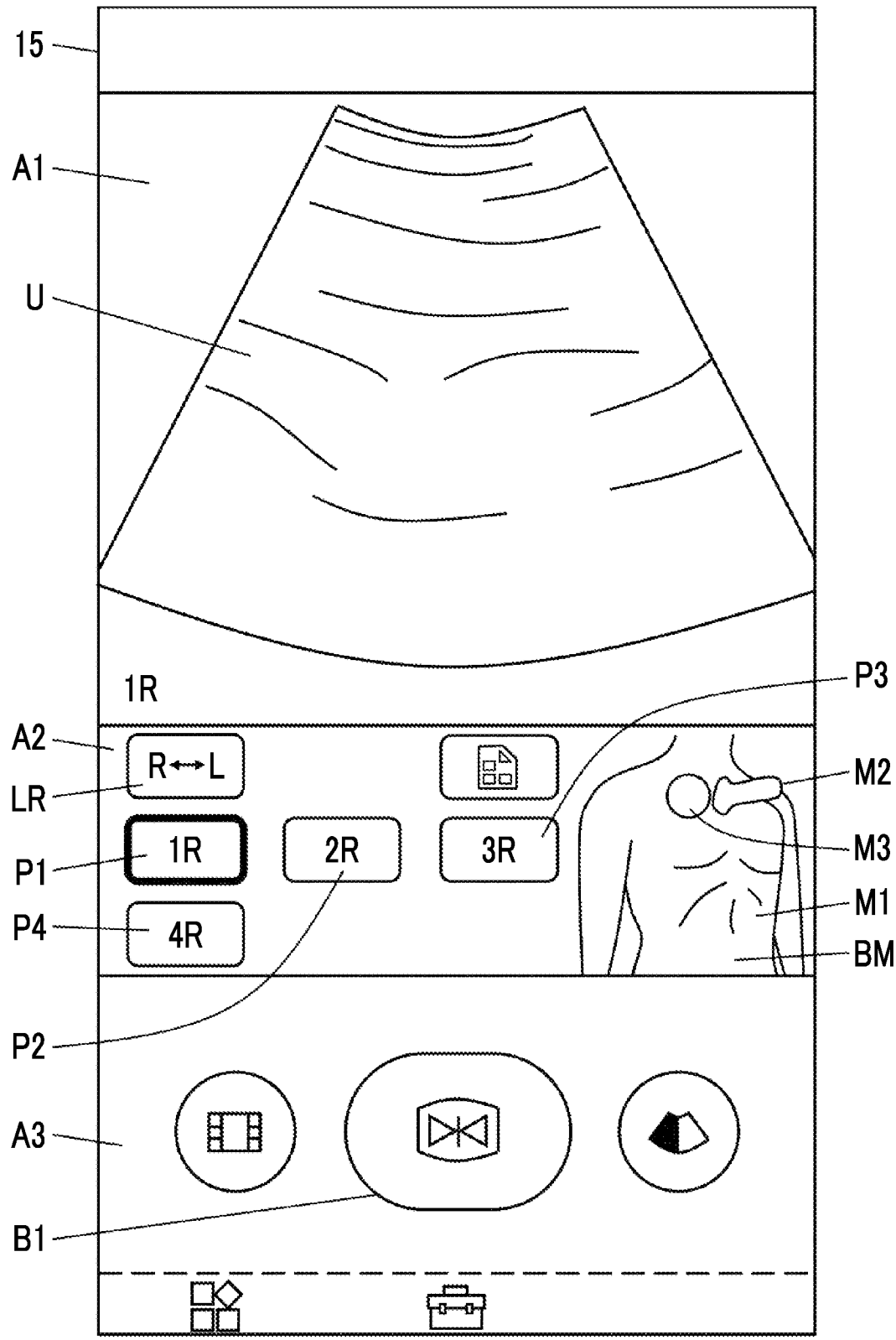
FIG. 7 is a diagram illustrating an example of a diagnostic location selection button and of an ultrasound image displayed on a monitor in Embodiment 1 of the present invention.

In addition, for example, as illustrated in FIG. 7, the monitor 15 has a first display region A1, a second display region A2, and a third display region A3.

The first display region A1 is a region for displaying an ultrasound image U.

The second display region A2 includes a left-right switching button LR for setting any of left and right lungs of the subject as the examination part, four examination location selection icons P1 to P4 for selecting an examination location of the subject, and a body mark BM. Each of the examination location selection icons P1 to P4 corresponds to an examination location of the lung of the subject. By tapping the left-right switching button LR, the examination location selection icons P1 to P4 are switched between "1R" to "4R" corresponding to examination locations of the right lung and "1L" to "4L" corresponding to examination locations of the left lung. In the example in FIG. 7, the examination location selection icons P1 to P4 correspond to the examination locations of the right lung registered under names "1R" to "4R", respectively.

In addition, the body mark BM includes a schematic diagram M1 representing a body part of the subject, a probe mark M2, and an examination location mark M3. Tapping the left-right switching button LR switches between the body mark BM including the schematic diagram M1 in which the right lung faces a front side, and the body mark BM including the schematic diagram M1 in which the left lung faces the front side. In the example in FIG. 7, the body mark BM including the schematic diagram M1 in which the right lung faces the front side is illustrated.

In the body mark BM, the probe mark M2 and the examination location mark M3 are disposed at positions corresponding to each of the examination location selection icons P1 to P4 on the schematic diagram M1 and visually indicate the examination location. In a case where any of the examination location selection icons P1 to P4 is tapped, the body mark BM corresponding to the tapped examination location selection icon P1 to P4 is displayed in the second display region A2 of the monitor 15.

The third display region A3 includes a user interface for inputting an instruction related to the operation of the ultrasound diagnostic apparatus 1, such as a freeze button B1 for freezing the ultrasound image U. Here, freezing the ultrasound image U means stopping generation of the ultrasound image U that is continuously generated by the image generation unit 13 and that is sequentially displayed on the monitor 15, and displaying the ultrasound image U of the most recent one frame on the monitor 15.

First, in step S1, the examination location for examining the lung of the subject is designated by the user through the input device 22, and the designated examination location is received by the body control unit 21. For example, in a case where the user selects the right lung as the examination part by tapping the left-right switching button LR and selects the examination location selection icon P1 corresponding to the examination location "1R" by tapping the examination location selection icon P1, the examination location "1R" is received by the body control unit 21. In a case where the examination location "1R" is received in such a manner, for example, a text "1R" is displayed in the first display region A1 of the monitor 15, and the body mark BM corresponding to the examination location "1R" is displayed in the second display region A2.

Next, in step S2, the user brings the ultrasound probe 2 into contact with a body surface of the subject. In this state, the ultrasound image U is captured.

At this point, the transmission and reception circuit 12, under control of the body control unit 21, generates the sound ray signal by performing the reception focus processing using the sound speed value set in advance. The sound ray signal generated by the transmission and reception circuit 12 in such a manner is transmitted to the image generation unit 13. The image generation unit 13 generates the ultrasound image U using the sound ray signal transmitted from the transmission and reception circuit 12.

In subsequent step S3, the ultrasound image U generated in step S2 is transmitted to the display control unit 14 and is displayed on the monitor 15. In addition, the ultrasound image U is stored in the image memory 16.

In step S4, the body control unit 21 determines whether or not a freeze instruction for the ultrasound image U is input by the user through the input device 22.

For example, in a case where the freeze button B1 displayed in the third display region A3 of the monitor 15 is tapped by the user, the body control unit 21 determines that the freeze instruction is provided. In addition, in a case where the freeze button B1 is not tapped by the user, the body control unit 21 determines that the freeze instruction is not provided.

In a case where it is determined that the freeze instruction is not provided, a return is made to step S2, and the ultrasound image U is newly captured. The ultrasound image U generated in this step S2 is displayed on the monitor 15 in subsequent step S3 and is stored in the image memory 16. In a case where step S3 is completed, a transition is made to step S4, and whether or not the ultrasound image U is frozen is determined.

By repeating step S2 to step S4 in such a manner, the ultrasound image U is continuously generated and displayed on the monitor 15. In addition, by repeating step S2 to step S4, the ultrasound images U of a plurality of frames are stored in the image memory 16.

In a case where it is determined that the freeze instruction is provided in step S4, the ultrasound image U is frozen by stopping the generation of the ultrasound image U and by displaying the ultrasound image U of the most recent frame on the monitor 15. Then, a transition is made to step S5.

In step S5, the similarity determination unit 18 determines similarity between a video image in a determined time until the freezing, that is, each of the ultrasound images U of the plurality of frames continuously generated within a determined time until the ultrasound image U is frozen, among the ultrasound images U of the plurality of frames stored in the image memory 16 by repeating step S2 to step S4 and the plurality of image patterns stored in the image pattern memory 17. Here, the determined time is set to, for example, a few seconds such as approximately one second to three seconds.

Here, for example, in a case where similarity between each of the image patterns corresponding to the four diagnostic findings of B-line, consolidation, normality, and absence of lung sliding and the ultrasound image U is calculated, the similarity can be determined for each of the diagnostic findings of B-line and consolidation using the ultrasound image U of one frame. However, for the diagnostic findings of normality and absence of lung sliding, since it is necessary to determine a motion of the boundary of the pleura in the ultrasound image U, it is preferable that the similarity is determined using the continuous ultrasound images U of the plurality of frames.

Thus, for the diagnostic finding of B-line, for example, the similarity determination unit 18 can calculate the similarity between each of the ultrasound images U of the plurality of frames generated in the determined time until the freezing and the image pattern corresponding to the diagnostic finding of B-line, and determine the similarity having the highest value among a plurality of calculated values of the similarity as the similarity for the diagnostic finding of B-line. In addition, for the diagnostic finding of consolidation, the similarity determination unit 18 can calculate the similarity between each of the ultrasound images U of the plurality of frames generated in the determined time until the freezing and the image pattern corresponding to the diagnostic finding of consolidation, and determine the similarity having the highest value among a plurality of calculated values of the similarity as the similarity for the diagnostic finding of consolidation.

Accordingly, the similarity determination unit 18 can obtain, as the final similarity, the similarity determined for the ultrasound image U in which the lung of the subject is clearly captured.

In addition, for the diagnostic finding of B-line, for example, the similarity determination unit 18 can also select the ultrasound image U including the largest number of linear patterns along the depth direction among the ultrasound images of the plurality of frames by analyzing the ultrasound images U of the plurality of frames generated in the determined time until the freezing, and determine the similarity between the selected ultrasound image U and the image pattern corresponding to the diagnostic finding of B-line.

In such a manner, the similarity determination unit 18 can determine the similarity using the ultrasound image U that best represents characteristics of the diagnostic finding for determining the similarity from the ultrasound images U of the plurality of frames generated in the determined time until the freezing. Accordingly, determination accuracy of the similarity can be improved.

In addition, for the diagnostic findings of normality and absence of lung sliding, it is preferable that the similarity is determined by considering the displacement of the boundary of the pleura. Thus, it is preferable that a plurality of continuous image patterns in which the boundary of the pleura is normally displaced are stored in the image pattern memory 17 as an image pattern corresponding to the diagnostic finding of normality, and a plurality of continuous image patterns in which the boundary of the pleura is almost not displaced are stored as an image pattern for the diagnostic finding of absence of lung sliding.

In this case, for the diagnostic finding of normality, the similarity determination unit 18 determines the similarity between the ultrasound images U of the plurality of frames generated in the determined time until the freezing and the plurality of image patterns corresponding to the diagnostic finding of normality. In addition, for the diagnostic finding of absence of lung sliding, the similarity determination unit 18 determines the similarity between the ultrasound images U of the plurality of frames generated in the determined time until the freezing and the plurality of image patterns corresponding to the diagnostic finding of consolidation.

In subsequent step S6, the display position changing unit 19 changes the display positions stored in advance for the diagnostic finding icons J1 to J4 corresponding to the plurality of diagnostic findings of which the similarity is determined in step S5, based on the similarity of the plurality of diagnostic findings determined in step S5.

For example, as illustrated in FIG. 4, it is assumed that the display position changing unit 19 stores the diagnostic finding icon J1 corresponding to the diagnostic finding of normality, the diagnostic finding icon J2 corresponding to the diagnostic finding of absence of lung sliding, the diagnostic finding icon J3 corresponding to the diagnostic finding of B-line, and the diagnostic finding icon J4 corresponding to the diagnostic finding of consolidation together with the display positions at which the diagnostic finding icons J1, J2, J3, and J4 are arranged in this order from the left. In a case where the similarity for each diagnostic finding is determined in step S5 such that values are decreased in order of B-line, consolidation, normality, and absence of lung sliding, the display position changing unit 19, for example, as illustrated in FIG. 5, can change the display positions of the diagnostic finding icons J1 to J4 in a descending order of the similarity such that the diagnostic finding icons J3, J4, J1, and J2 are arranged in this order from the left.

Figure 8:
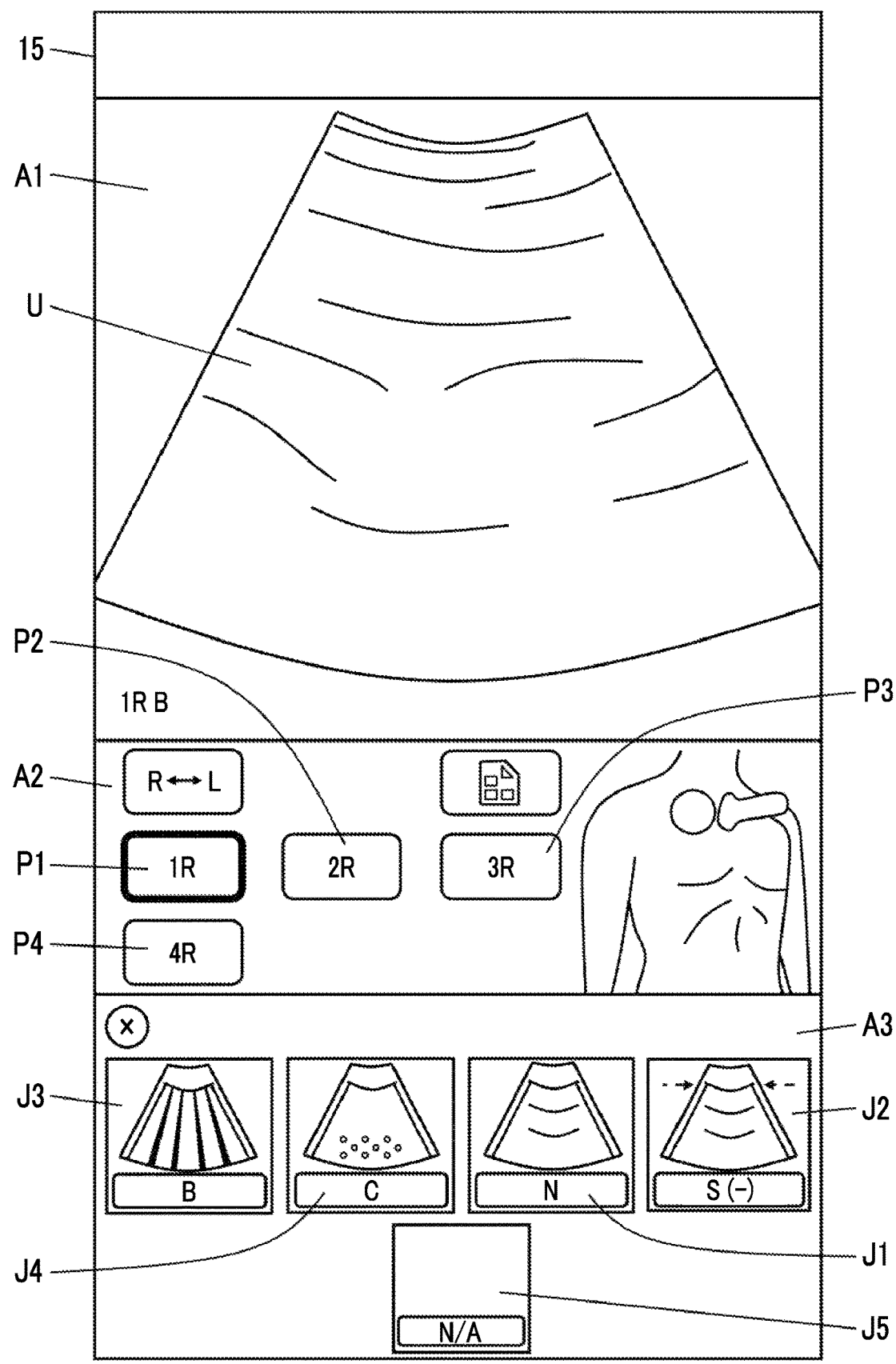
FIG. 8 is a diagram illustrating an example of the plurality of diagnostic finding icons displayed on the monitor in Embodiment 1 of the present invention.

In step S7, for example, as illustrated in FIG. 8, the diagnostic finding icons J1 to J4 are displayed in the third display region A3 of the monitor 15 in accordance with the display positions changed in step S6 under control of the display control unit 14. In the example in FIG. 8, the diagnostic finding icons J1 to J4 are displayed on the monitor 15 in an order of the diagnostic finding icon J3 corresponding to the diagnostic finding of B-line, the diagnostic finding icon J4 corresponding to the diagnostic finding of consolidation, the diagnostic finding icon J1 corresponding to the diagnostic finding of normality, and the diagnostic finding icon J2 corresponding to the diagnostic finding of absence of lung sliding from the left. In addition, in the example in FIG. 8, a diagnostic finding icon J5 representing that none of the diagnostic findings is applicable is displayed below the diagnostic finding icons J1 to J4.

Accordingly, the diagnostic finding icons J1 to J4 are displayed on the monitor 15 in accordance with the display positions based on the similarity determined in step S5. Thus, even in a case where the user is not familiar with diagnosis of the subject, the user can easily assign an appropriate diagnostic finding to the ultrasound image U displayed on the monitor 15 by checking a display order of the diagnostic finding icons J1 to J4.

In step S8, the body control unit 21 receives the diagnostic finding icon selected by the user through the input device 22 among the diagnostic finding icons J1 to J4 displayed on the monitor 15.

In subsequent step S9, the diagnostic finding linking unit 20 links the ultrasound image U used for the determination of the similarity in step S5 to the diagnostic finding corresponding to the diagnostic finding icon selected by the user in step S8.

For example, in a case where the highest similarity in the similarity determined for the ultrasound images U of the plurality of frames is determined as the final similarity for each of the diagnostic findings of B-line and consolidation, the diagnostic finding linking unit 20 selects the ultrasound image U of the highest similarity for each of the diagnostic findings of B-line and consolidation as a target to be linked.

In addition, for each of the diagnostic findings of normality and absence of lung sliding, the diagnostic finding linking unit 20 sets the ultrasound images U of the plurality of frames generated in the determined time until the freezing as a target to be linked.

Last, in step S10, the diagnostic finding corresponding to the diagnostic finding icon received in step S8 is displayed on the monitor 15 under control of the display control unit 14. In the example in FIG. 8, the diagnostic finding icon J3 displayed at the left end is selected by the user among the four diagnostic finding icons J1 to J4, and the diagnostic finding "B" corresponding to the diagnostic finding icon J3 is displayed in the first display region A1 together with the ultrasound image U linked to the diagnostic finding of B-line in step S9.

From the above, according to the ultrasound diagnostic apparatus 1 according to Embodiment 1 of the present invention, the similarity between the ultrasound image U and each of the plurality of image patterns corresponding to the plurality of determined diagnostic findings is determined. The display positions of the plurality of diagnostic finding icons J1 to J4 corresponding to the plurality of diagnostic findings are changed based on the similarity. The diagnostic finding icons J1 to J4 are displayed on the monitor 15 in accordance with the changed display positions. Thus, the user can easily assign an appropriate diagnostic finding to the ultrasound image U displayed on the monitor 15 by checking the display positions of the diagnostic finding icons J1 to J4.

As illustrated in FIG. 1, in the ultrasound diagnostic apparatus 1, while the transmission and reception circuit 12 is comprised in the ultrasound probe 2, the transmission and reception circuit 12 may be comprised in the diagnostic apparatus body 3 instead of being comprised in the ultrasound probe 2.

In addition, while the image generation unit 13 is comprised in the diagnostic apparatus body 3, the image generation unit 13 may be comprised in the ultrasound probe 2 instead of being comprised in the diagnostic apparatus body 3.

In addition, as illustrated in FIG. 3, while the image generation unit 13 comprises the signal processing unit 35, the DSC 36, and the image processing unit 37, the signal processing unit 35 can be included in the ultrasound probe 2.

In addition, a connection method between the ultrasound probe 2 and the diagnostic apparatus body 3 is not particularly limited and may be wired connection or wireless connection.

In addition, the diagnostic apparatus body 3 may be of a so-called handheld type that can be easily carried by the user, or may be of a so-called stationary type.

In addition, while the four examination location selection icons P1 to P4 are illustrated in FIG. 7, the number of examination location selection icons P1 to P4 is not limited to four. For example, the body control unit 21 can store the number of examination locations and a set of corresponding examination locations. In this case, the stored number of examination locations can be selected by the input operation of the user through the input device 22, and the number of examination location selection icons identical to the number of examination locations selected by the user can be displayed in the second display region A2 of the monitor 15 under control of the display control unit 14. By switching the number of examination locations in such a manner, the present invention can be applied to a wider variety of examinations.

In addition, while using the video image as the ultrasound diagnosis image to be used in the determination of the similarity in step S5 is described, it is also possible to use only the still image of one frame. In a case of using only the still image of one frame, the similarity determination unit 18, for example, can determine the similarity between the ultrasound image U of one frame displayed on the monitor 15 at the time of freezing and the image patterns corresponding to the plurality of diagnostic findings. However, in order to accurately determine the similarity for the diagnostic findings of normality and absence of lung sliding, it is preferable that the similarity is determined using the video image.

In addition, in the diagnostic finding of normality, it is known that tissues from the boundary of the pleura to a certain depth position are displaced in accordance with exhalation and inhalation of the subject. Thus, for example, in a case of determining the similarity for the diagnostic findings of normality and absence of lung sliding, the similarity determination unit 18 can determine the similarity by considering a motion of an image between the boundary of the pleura included in the ultrasound image U and the certain depth position from the boundary of the pleura. Accordingly, accuracy with which the similarity for the diagnostic findings of normality and absence of lung sliding is determined can be improved.

A depth position of the artifact that is caused by multiple reflection of the ultrasound waves and that extends along the direction orthogonal to the depth direction may be set as the certain depth position.

In addition, while the diagnostic finding linking unit 20 is described as using the ultrasound images U of the plurality of frames generated in the determined time until the freezing as a target to be linked for each of the diagnostic findings of normality and absence of lung sliding in step S9, it is also possible to use the ultrasound image U of one frame as a target to be linked. For example, in a case where an image pattern related to the boundary of the pleura is stored in the image pattern memory 17, and the similarity for the boundary of the pleura in the ultrasound images U of the plurality of frames is determined by the similarity determination unit 18 in step S5, the diagnostic finding linking unit 20 can use, as a target to be linked, the ultrasound image U of a frame of the highest similarity related to the boundary of the pleura among the ultrasound images U of the plurality of frames generated in the determined time until the freezing.

In addition, while the four diagnostic finding icons J1 to J4 are illustrated, the number of diagnostic finding icons is not limited to four and can be set to, for example, two, three, or five or more in accordance with the number of diagnostic findings for determining the similarity. However, it is preferable that at least one of the plurality of diagnostic findings related to the lung of the subject includes the diagnostic finding of any of B-line, consolidation, normality, and absence of lung sliding.

Figure 9:
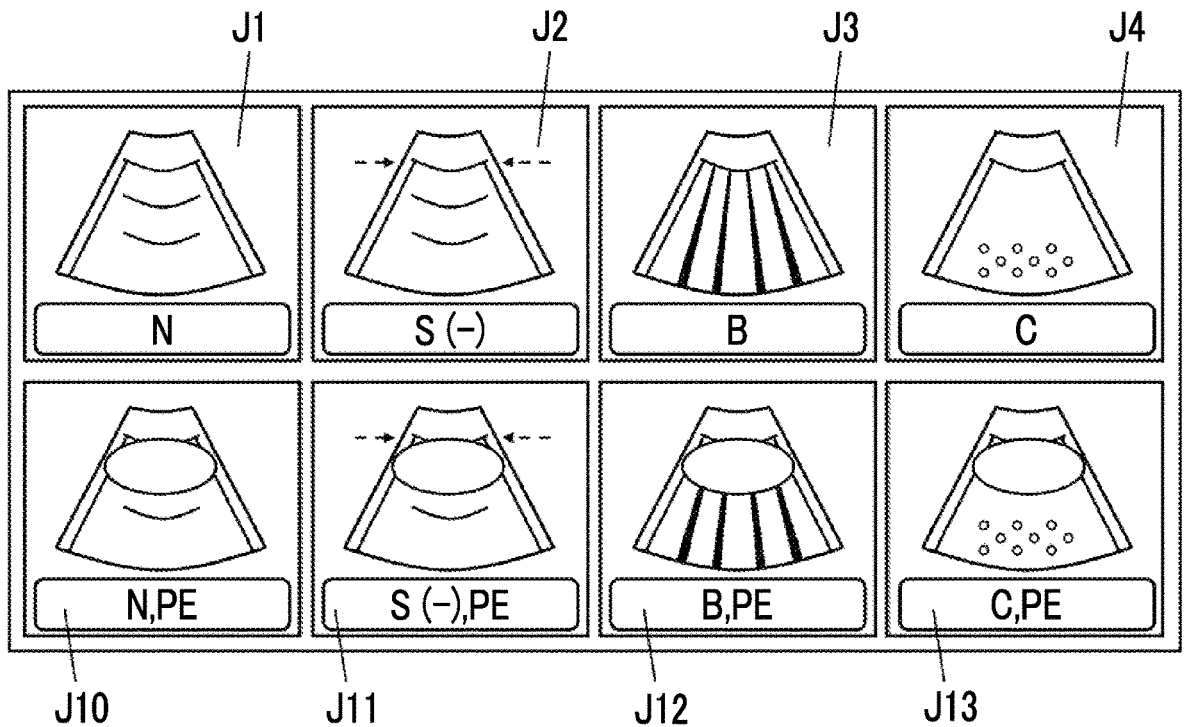
FIG. 9 is another example of the diagnostic finding icons in Embodiment 1 of the present invention.

For example, in a case of considering a diagnostic finding caused by accumulation of so-called pleural effusion (PE) in the lung of the subject, total eight diagnostic findings including accumulation of pleural effusion (N, PE), absence of lung sliding and accumulation of pleural effusion (S(-), PE), B-line and accumulation of pleural effusion (B, PE), and consolidation and accumulation of pleural effusion (C, PE) in addition to the diagnostic findings of normality, absence of lung sliding, B-line, and consolidation are considered. In this case, for example, eight diagnostic finding icons J1 to J4 and J10 to J13 corresponding to the eight diagnostic findings as illustrated in FIG. 9 are displayed on the monitor 15.

Figure 10:
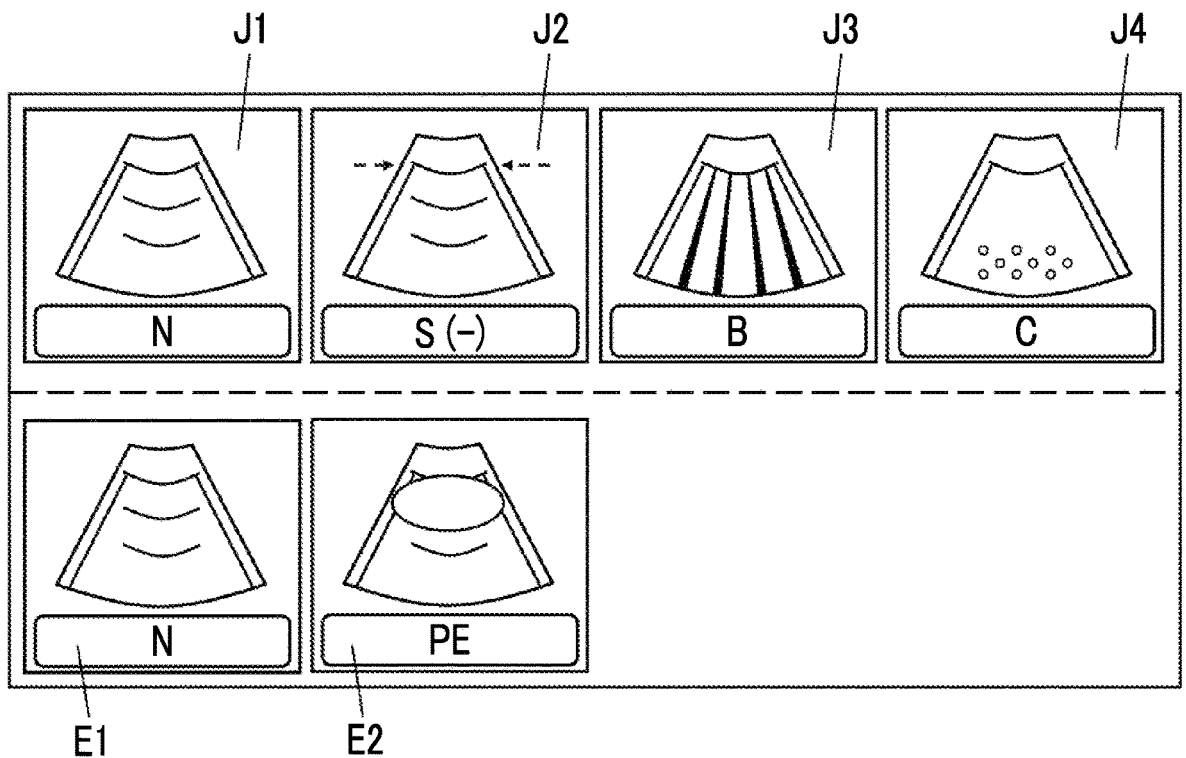
FIG. 10 is an example of pleural effusion presence or absence icons displayed together with the diagnostic finding icons in Embodiment 1 of the present invention.

In addition, in a case where the diagnostic finding of accumulation of pleural effusion is considered, it is also possible to display, for example, as illustrated in FIG. 10, the diagnostic finding icons J1 to J4 corresponding to the diagnostic findings of normality, absence of lung sliding, B-line, and consolidation, a pleural effusion presence or absence icon E1 representing that accumulation of pleural effusion is not recognized, and a pleural effusion presence or absence icon E2 representing that accumulation of pleural effusion is recognized. In this case, the user can assign the diagnostic finding in which presence or absence of accumulation of pleural effusion is considered, to the ultrasound image U by selecting any of the diagnostic finding icons J1 to J4 through the input device 22 and then, by selecting any of the pleural effusion presence or absence icons E1 and E2.

Six icons of the diagnostic finding icons J1 to J4 and the pleural effusion presence or absence icons E1 and E2 may not be displayed at the same time on the monitor 15. For example, it is also possible to display only the four diagnostic finding icons J1 to J4 on the monitor 15 among the six icons of the diagnostic finding icons J1 to J4 and the pleural effusion presence or absence icons E1 and E2, and to display the pleural effusion presence or absence icons E1 and E2 on the monitor 15 in a case where any one of the four diagnostic finding icons J1 to J4 is selected by the user. By performing such display, it is possible to clearly show the user that the pleural effusion presence or absence icon E1 or E2 is selected after any of the four diagnostic finding icons J1 to J4 is selected, and the user can more smoothly assign the diagnostic finding to the ultrasound image U.

Figure 11:
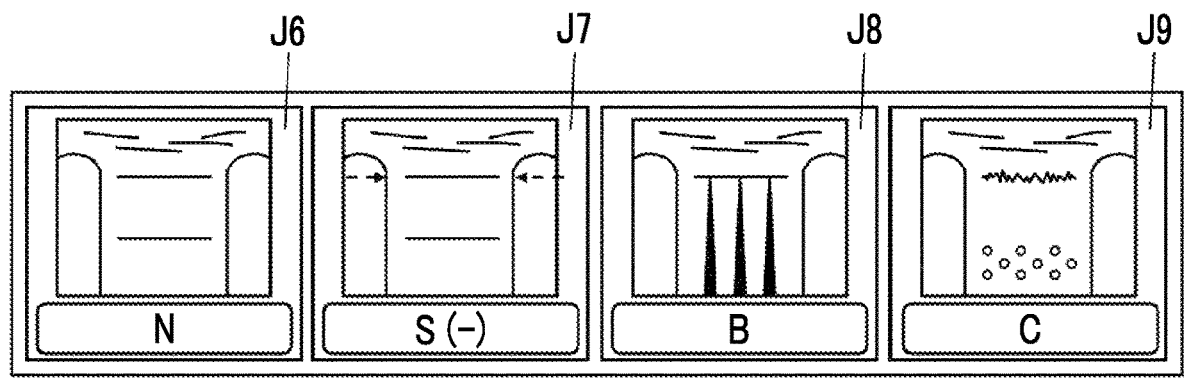
FIG. 11 is a diagram illustrating an example of diagnostic finding icons corresponding to a linear type ultrasound probe in Embodiment 1 of the present invention.

In addition, while the diagnostic finding icons J1 to J4 having designs corresponding to the ultrasound image U captured by the ultrasound probe 2 of a so-called convex type are illustrated in FIG. 4, FIG. 5, and FIG. 8 to FIG. 10, the designs of the diagnostic finding icons J1 to J4 may be set in accordance with the type of the ultrasound probe 2 used for examination of the subject. For example, as illustrated in FIG. 11, diagnostic finding icons J6 to J9 having designs corresponding to the ultrasound image U captured by the ultrasound probe 2 of a so-called linear type are illustrated. The diagnostic finding icon J6 corresponds to the diagnostic finding of normality. The diagnostic finding icon J7 corresponds to the diagnostic finding of absence of lung sliding. The diagnostic finding icon J8 corresponds to the diagnostic finding of B-line. The diagnostic finding icon J9 corresponds to the diagnostic finding of consolidation.

Figure 12:
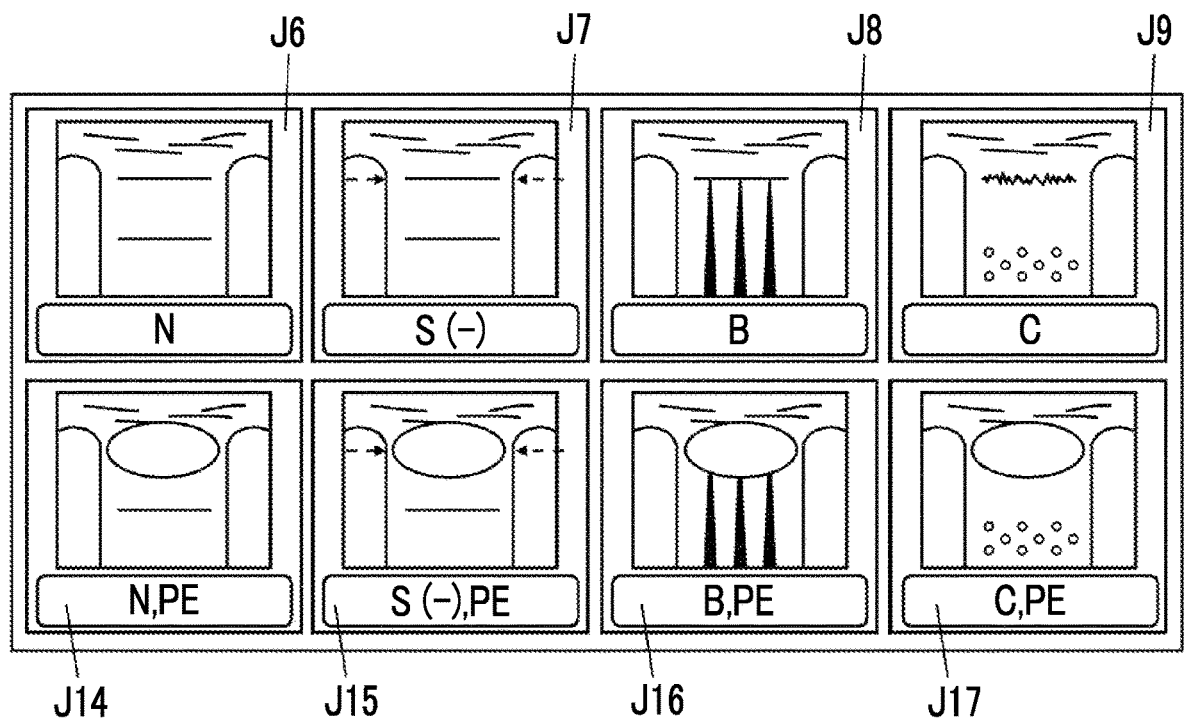
FIG. 12 is a diagram illustrating another example of the diagnostic finding icons corresponding to the linear type ultrasound probe in Embodiment 1 of the present invention.

In addition, even in a case of using the ultrasound probe 2 of the linear type is used, diagnostic finding icons J14 to J17 in which accumulation of pleural effusion is considered as illustrated in FIG. 12 can be displayed on the monitor 15 as in the case of using the ultrasound probe 2 of the convex type. In the example in FIG. 12, the diagnostic finding icons J14 to J17 having designs corresponding to the ultrasound probe 2 of the linear type are illustrated.

In addition, while illustration is not provided, it is also possible to display a pleural effusion presence or absence icon having a design corresponding to the ultrasound probe 2 of the linear type on the monitor 15 as in the aspect illustrated in FIG. 10.

In addition, while illustration is not provided, in a case where the ultrasound probe 2 of a so-called sector type is used, a diagnostic finding icon having a design corresponding to the ultrasound probe 2 of the sector type can be set.

Figure 6:
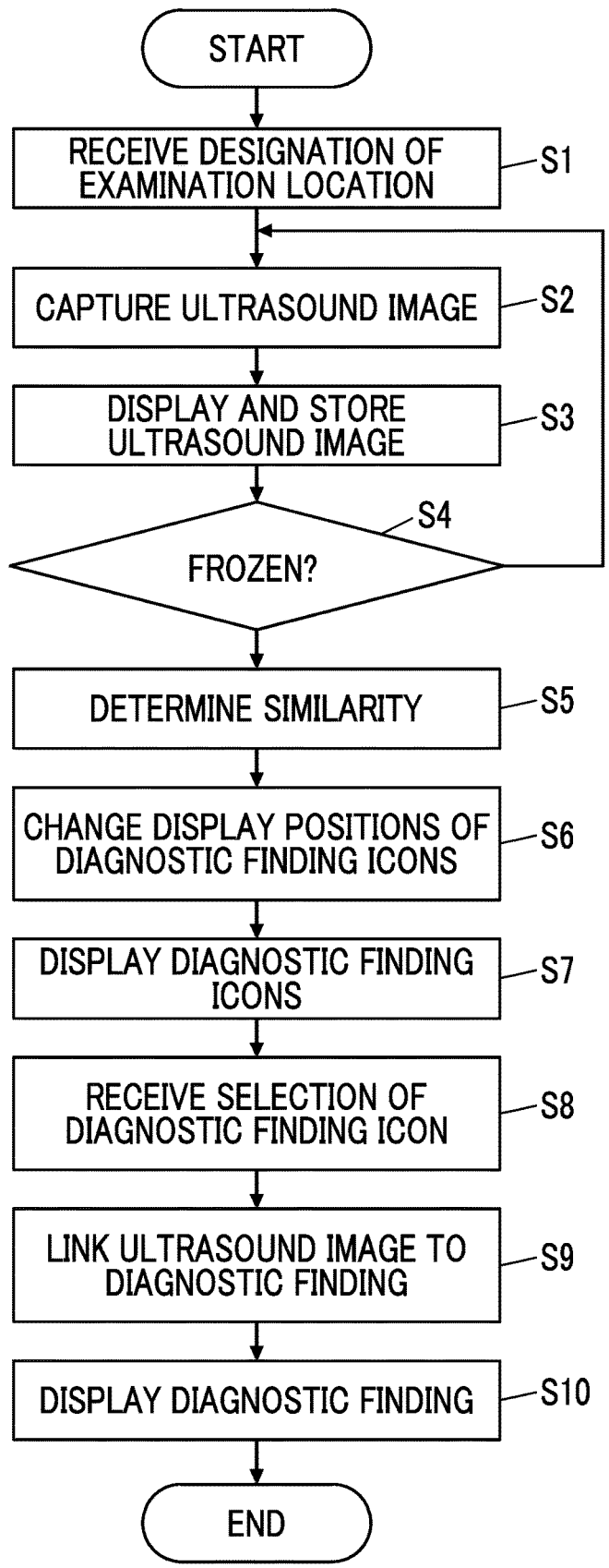
FIG. 6 is a flowchart illustrating an operation of the ultrasound diagnostic apparatus in Embodiment 1 of the present invention.

In addition, while an example of examining the lung of the subject is described in the operation of the ultrasound diagnostic apparatus 1 of Embodiment 1 using the flowchart in FIG. 6, the present invention is not limited to the examination of the lung and can be applied to various examination parts of the subject.

Figure 13:
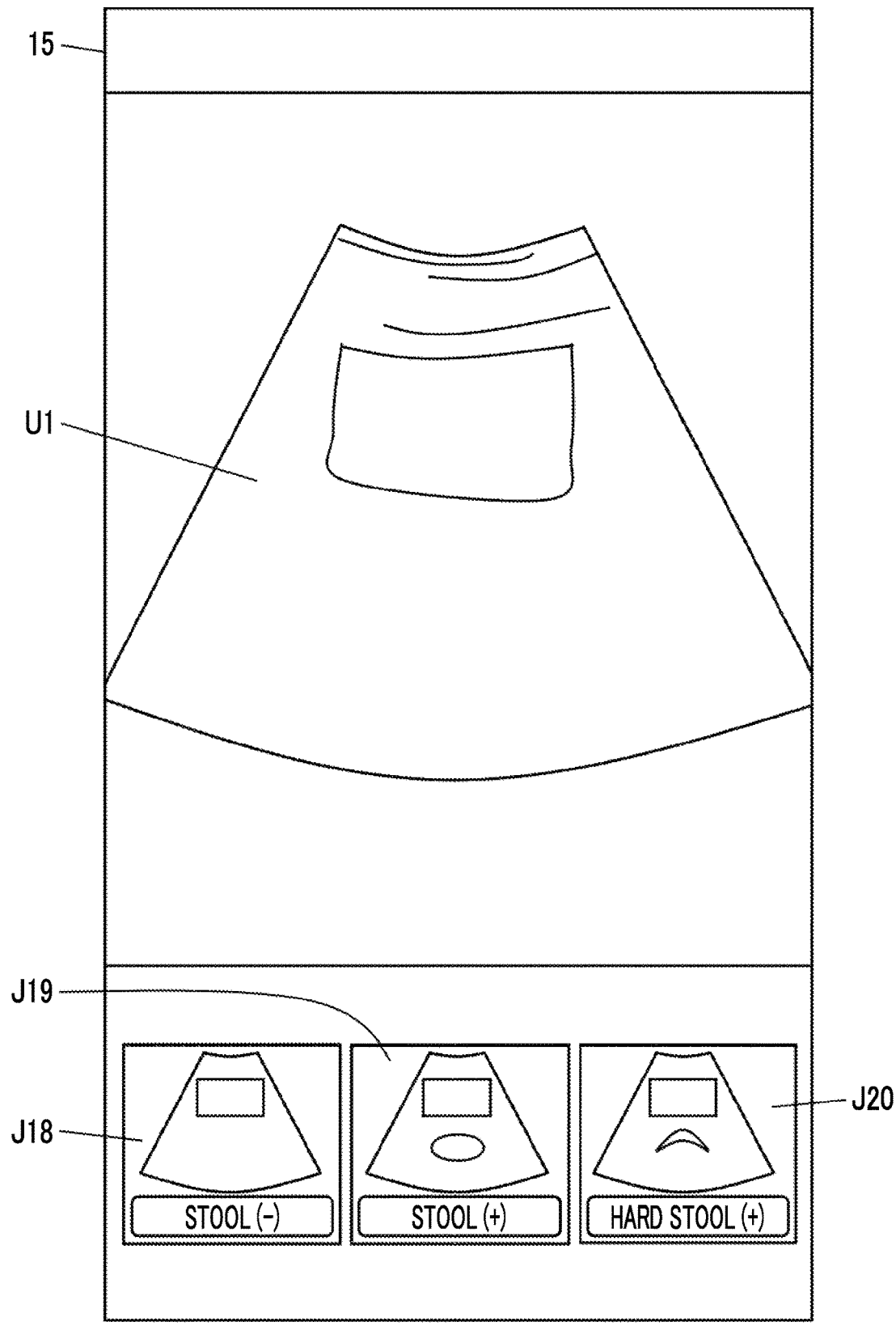
FIG. 13 is another example of the ultrasound image and of the diagnostic finding icons displayed on the monitor in Embodiment 1 of the present invention.

For example, the present invention can be applied to examination of a rectum of the subject. In this case, for example, diagnostic findings of loose stool, standard stool, and hard stool are set in accordance with hardness of a stool inside the rectum. As illustrated in FIG. 13, a diagnostic finding icon J18 corresponding to the diagnostic finding of loose stool, a diagnostic finding icon J19 corresponding to the diagnostic finding of standard stool, and a diagnostic finding icon J20 corresponding to the diagnostic finding of hard stool are displayed on the monitor 15. In the example in FIG. 13, the three diagnostic finding icons J18 to J20 are displayed on the monitor 15 together with an ultrasound image U1 obtained by imaging the rectum of the subject.

In addition, for example, the present invention can also be applied to examination of an inferior vena cava of the subject. In this case, for example, based on a size of a diameter of the inferior vena cava and on presence or absence of a respiratory change in the diameter of the inferior vena cava, six diagnostic findings of large diameter of inferior vena cava and presence of respiratory change in diameter of inferior vena cava, large diameter of inferior vena cava and absence of respiratory change in diameter of inferior vena cava, normal diameter of inferior vena cava and presence of respiratory change in diameter of inferior vena cava, normal diameter of inferior vena cava and absence of respiratory change in diameter of inferior vena cava, small diameter of inferior vena cava and presence of respiratory change in diameter of inferior vena cava, and small diameter of inferior vena cava and absence of respiratory change in diameter of inferior vena cava are set as a diagnostic finding.

Here, "large diameter of inferior vena cava" means that the diameter of the inferior vena cava is greater than or equal to 20 mm. In addition, "normal diameter of inferior vena cava" means that the diameter of the inferior vena cava is greater than 10 mm and less than 20 mm. In addition, "small diameter of inferior vena cava" means that the diameter of the inferior vena cava is less than or equal to 10 mm. In addition, "presence of respiratory change in diameter of inferior vena cava" means that a change in the diameter of the inferior vena cava in exhalation is greater than 40% and less than or equal to 50%. In addition, "absence of respiratory change in diameter of inferior vena cava" means that a change in the diameter of the inferior vena cava in exhalation is less than or equal to 40%.

In addition, for example, the present invention can also be applied to examination of a liver of the subject. In this case, for example, diagnostic findings of normality, liver cyst, fatty liver, liver hemangioma, and calcification in liver can be set as a diagnostic finding.

In addition, for example, the present invention can also be applied to examination of a gallbladder of the subject. In this case, for example, diagnostic findings of normality, gallbladder polyp, stone in gallbladder wall, gallstone, gallbladder adenomyomatosis, and gallbladder wall thickening can be set as a diagnostic finding.

In addition, for example, the present invention can also be applied to examination of a kidney of the subject. In this case, for example, diagnostic findings of normality, calcification in kidney, kidney stone, cystic kidney, renal angiomyolipoma, hydronephrosis, duplicated ureter, and kidney cyst can be set as a diagnostic finding.

In addition, for example, the present invention can also be applied to examination of a heart of the subject. In this case, for example, based on contractility of a left ventricle, diagnostic findings of severe decrease in contractility, decrease in contractility, normality, and hypercontraction can be set as a diagnostic finding. Here, "severe decrease in contractility" is a diagnostic finding indicating that a left ventricular ejection fraction calculated by (amount of blood pumped from left ventricle once)/(end-diastolic volume of left ventricle)×100=[(maximum volume of left ventricle)−(minimum volume of left ventricle)]/(maximum volume of left ventricle) is less than or equal to 30%. In addition, "decrease in contractility" is a diagnostic finding indicating that the left ventricular ejection fraction is greater than 30% and less than or equal to 55%. In addition, "normality" is a diagnostic finding indicating that the left ventricular ejection fraction is greater than 55% and less than 70%. In addition, "hypercontraction" is a diagnostic finding indicating that the left ventricular ejection fraction is greater than or equal to 70%.

For example, the volume of the left ventricle can be calculated by measuring a width of the left ventricle in three directions orthogonal to each other from the ultrasound images U corresponding to two cross sections of the left ventricle orthogonal to each other and by using a value of the measured width.

While the present invention can be applied to various examination parts of the subject in such a manner, the examination part of the subject can be set by, for example, the input operation of the user through the input device 22. Accordingly, the user can easily assign an appropriate diagnostic finding to the ultrasound image U in examination of various examination parts of the subject.

In addition, while an example in which the display position changing unit 19 changes the display positions of the four diagnostic finding icons J1 to J4 such that the diagnostic finding icon disposed at the left end corresponds to the diagnostic finding of the highest similarity is illustrated in step S6, it is also possible to change the display positions of the four diagnostic finding icons J1 to J4 such that the diagnostic finding icon disposed at the right end corresponds to the diagnostic finding of the highest similarity.

However, in a case where the diagnostic apparatus body 3 is of the so-called handheld type, the user generally holds the ultrasound probe 2 in a right hand and holds the diagnostic apparatus body 3 in a left hand. Thus, by arranging the diagnostic finding icons J1 to J4 such that the diagnostic finding icon disposed at the left end corresponds to the diagnostic finding of the highest similarity, the diagnostic finding icon corresponding to the diagnostic finding of the highest similarity is easily selected. Thus, in a case where the diagnostic apparatus body 3 is of the handheld type, it is preferable that the display positions of the four diagnostic finding icons J1 to J4 are changed such that the diagnostic finding icon disposed at the left end corresponds to the diagnostic finding of the highest similarity.

Figure 14:
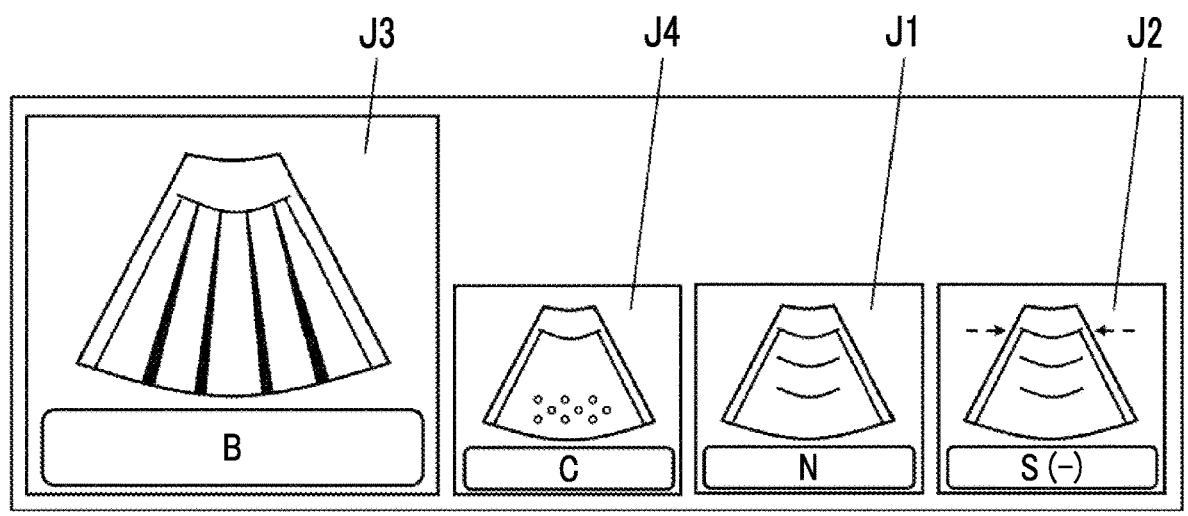
FIG. 14 is a diagram illustrating another display example of the diagnostic finding icons in Embodiment 1 of the present invention.

In addition, in step S6, the display position changing unit 19 can change the display positions of the plurality of diagnostic finding icons J1 to J4 such that the plurality of diagnostic finding icons J1 to J4 are arranged in a descending of the similarity determined in step S5, and furthermore, as illustrated in FIG. 14, can display the diagnostic finding icon corresponding to the diagnostic finding of the highest similarity to be larger than the other diagnostic finding icons on the monitor 15. In the example in FIG. 14, the diagnostic finding icon J3 corresponding to B-line is disposed leftmost and is displayed to be larger than the diagnostic finding icons J1, J2, and J4.

Accordingly, the diagnostic finding icon corresponding to the diagnostic finding of the highest similarity stands out, and it is possible to clearly show the user that the similarity of the diagnostic finding corresponding to this diagnostic finding icon is the highest.

In addition, for example, the display position changing unit 19 can also change the display positions of the plurality of diagnostic finding icons J1 to J4 and furthermore, change sizes of the diagnostic finding icons J1 to J4 in accordance with the respective diagnostic findings. For example, the display position changing unit 19 can increase the size of the diagnostic finding icon as the diagnostic finding icon corresponds to the diagnostic finding of higher similarity, and decrease the size of the diagnostic finding icon as the diagnostic finding icon corresponds to the diagnostic finding of lower similarity.

In addition, in changing the sizes of the diagnostic finding icons J1 to J4, for example, a diagnostic finding icon corresponding to the diagnostic finding of the lowest similarity can be removed from the monitor 15. Particularly, in a case where the diagnostic apparatus body 3 is of the handheld type, the monitor 15 is small. Thus, by removing the diagnostic finding icon corresponding to the diagnostic finding of the lowest similarity from the monitor 15, a diagnostic finding icon corresponding to a diagnostic finding of relatively high similarity can be displayed to be large, and the user easily selects the diagnostic finding icon.

Embodiment 2

In the operation description of the ultrasound diagnostic apparatus 1 using the flowchart in FIG. 6, the similarity for the plurality of diagnostic findings is described as being determined in step S5 using the ultrasound images U of the plurality of frames generated in the determined time until the freezing based on a determination that the freeze instruction is provided in step S4 as a trigger. However, the ultrasound image U to be used for the determination of the similarity can also be manually selected by the user.

Figure 15:
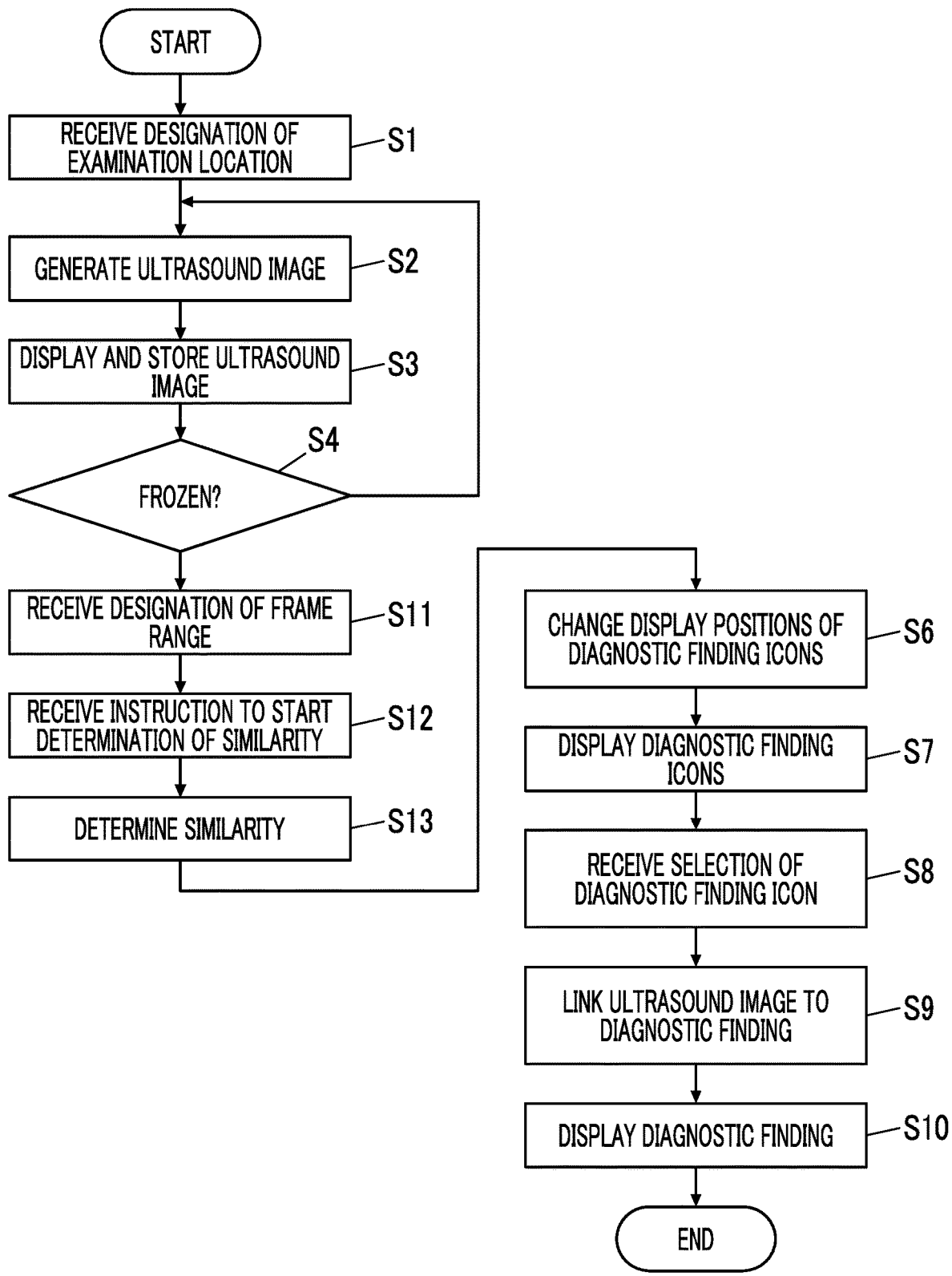
FIG. 15 is a flowchart illustrating an operation of an ultrasound diagnostic apparatus in Embodiment 2 of the present invention.

An operation of the ultrasound diagnostic apparatus 1 in Embodiment 2 will be described using the flowchart illustrated in FIG. 15. In the flowchart in FIG. 15, step S11 to step S13 are provided instead of step S5 in the flowchart in FIG. 6 in Embodiment 1.

Step S1 to step S4 are identical to step S1 to step S4 in the flowchart in FIG. 6 and thus, will not be described in detail.

In step S4, in a case where it is determined that the freeze instruction is provided, a transition is made to step S11.

In step S11, a frame range of the ultrasound images U of the plurality of frames to be used for the determination of the similarity is designated by the user through the input device 22, and the designated frame range is received by the body control unit 21.

Figure 16:
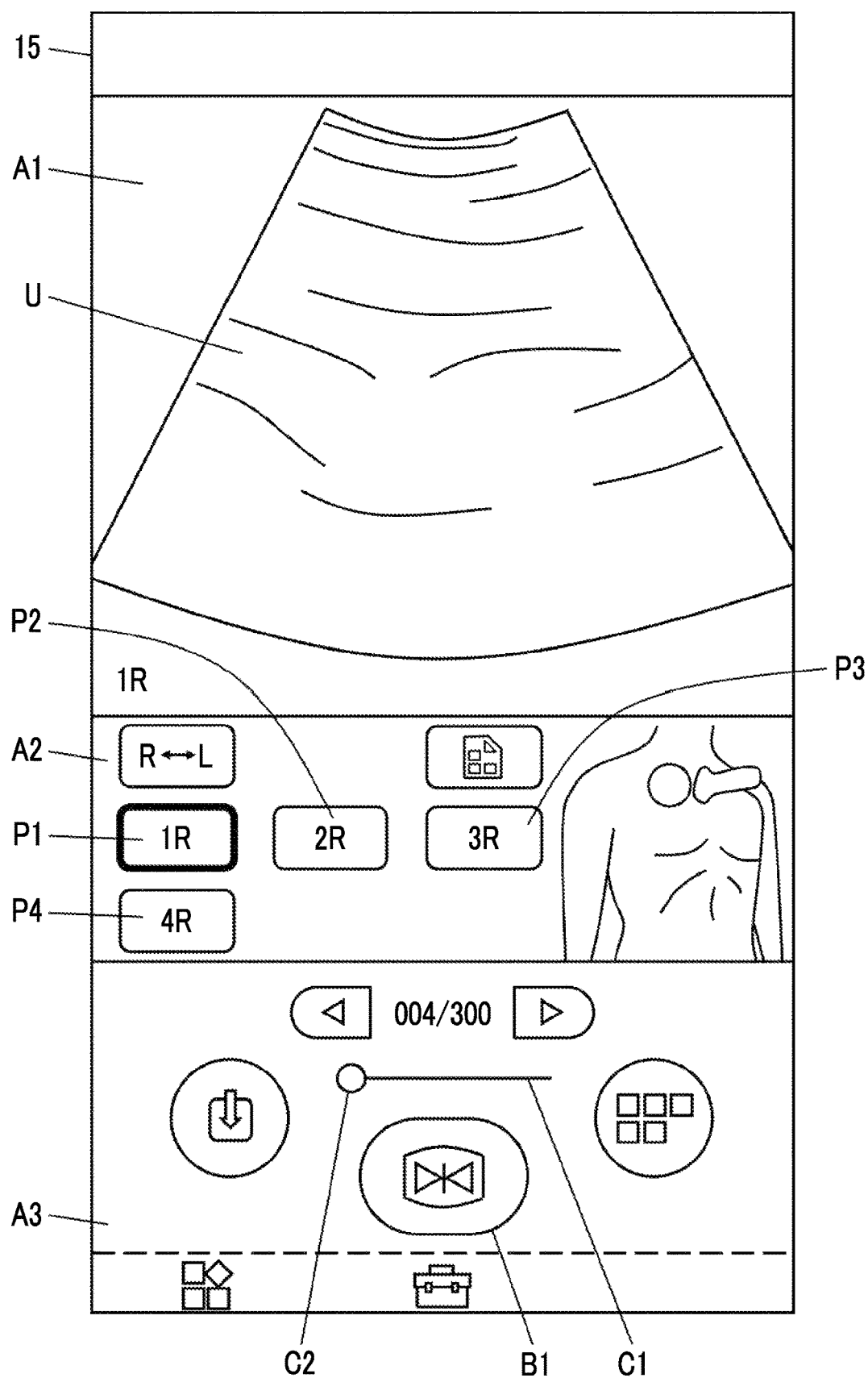
FIG. 16 is a diagram illustrating a slide bar displayed on a monitor in Embodiment 2 of the present invention.

At this point, for example, as illustrated in FIG. 16, a slide bar C1 for designating the frame range and the freeze button B1 are displayed in the third display region A3 of the monitor 15 under control of the display control unit 14. The slide bar C1 includes a slide button C2 for selecting the ultrasound image U of one frame among the ultrasound images U of the plurality of frames generated from the start of the examination of the subject until the freezing by causing the user to drag the slide button C2 to slide between both ends of the slide bar C1. The left end of the slide bar C1 corresponds to the ultrasound image U that is generated first after the start of the examination of the subject. The right end of the slide bar C1 corresponds to the most recent ultrasound image U at the time of freezing. The ultrasound image U corresponding to a position of the slide button C2 is displayed in the first display region A1 of the monitor 15.

For example, the ultrasound image U of the first frame of the frame range to be used for the determination of the similarity is designated by causing the user to slide the slide button C2 and tap the freeze button B1 in a state where the slide button C2 is moved to a first position. The ultrasound image U of the last frame of the frame range to be used for the determination of the similarity is designated by causing the user to further slide the slide button C2 and tap the freeze button B1 again in a state where the slide button C2 is moved to a second position. For example, the frame range is designated in such a manner, and the designated frame range is received by the body control unit 21.

In subsequent step S12, an instruction to start the determination of the similarity is input by the user through the input device 22, and this instruction is received by the body control unit 21.

In step S13, the similarity determination unit 18 determines the similarity between the ultrasound images U of the plurality of frames within the frame range designated by the user in step S11 and the plurality of image patterns corresponding to the plurality of diagnostic findings stored in the image pattern memory 17.

In subsequent step S6, the display position changing unit 19 changes the display positions of the plurality of diagnostic finding icons J1 to J4 based on the similarity determined for each of the plurality of diagnostic findings in step S13.

In step S7, the plurality of diagnostic finding icons J1 to J4 are displayed on the monitor 15 based on the display positions changed in step S6.

In step S8, one diagnostic finding icon of the plurality of diagnostic finding icons J1 to J4 displayed on the monitor 15 is selected by the user, and the selected diagnostic finding icon is received by the body control unit 21.

In step S9, the diagnostic finding linking unit 20 links the ultrasound image U used for the determination of the similarity in step S13 to the diagnostic finding corresponding to the diagnostic finding icon selected in step S8.

Last, in step S10, the diagnostic finding linked to the ultrasound image U in step S9 is displayed on the monitor 15.

From the above, even in a case where the frame range of the ultrasound images U of the plurality of frames to be used for the determination of the similarity is manually designated by the user, the user can easily assign an appropriate diagnostic finding to the ultrasound image U displayed on the monitor 15 by checking the display positions of the diagnostic finding icons J1 to J4 as in Embodiment 1.

While the frame range of the ultrasound images U of the plurality of frames to be used for the determination of the similarity is described as being designated by the user through the input device 22 among the ultrasound images U of the plurality of frames generated from the start of the examination of the subject until the freezing, only the ultrasound image U of one frame may be designated instead of the designation of the frame range.

For example, by causing the user to move the slide button C2 and tap the freeze button B1 in a state where the ultrasound image U of a desired frame is displayed on the monitor 15, the ultrasound image U of the frame displayed on the monitor 15 is designated as the ultrasound image U to be used for the determination of the similarity.

EXPLANATION OF REFERENCES

1: ultrasound diagnostic apparatus
2: ultrasound probe
3: diagnostic apparatus body
11: transducer array
12: transmission and reception circuit
13: image generation unit
14: display control unit
15: monitor
16: image memory
17: image pattern memory
18: similarity determination unit
19: display position changing unit
20: diagnostic finding linking unit
21: body control unit
22: input device
23: processor
31: pulser
32: amplification unit
33: AD conversion unit
34: beam former
35: signal processing unit
36: DSC
37: image processing unit
A1: first display region
A2: second display region
A3: third display region
B1: freeze button
BM: body mark
C1: slide bar
C2: slide button
E1, E2: pleural effusion presence or absence icon
J1 to J20: diagnostic finding icon
LR: left-right switching button
M1: schematic diagram
M2: probe mark
M3: examination location mark
P1 to P4: examination location selection icon
U, U1: ultrasound image

What is claimed is:

1. An ultrasound diagnostic apparatus comprising:
an ultrasound probe; and
a diagnostic apparatus body connected to the ultrasound probe,
wherein the diagnostic apparatus body includes
a monitor, and
a processor configured to
display an ultrasound diagnosis image at a time of freezing and a plurality of diagnostic finding icons corresponding to a plurality of determined diagnostic findings on the monitor,
determine similarity between ultrasound diagnosis images of a plurality of frames constituting a video image in a determined time until freezing and each of a plurality of image patterns corresponding to the plurality of diagnostic findings,
determine a maximum similarity among a plurality of similarities determined from the ultrasound diagnosis images of the plurality of frames as a final similarity, for each of the image patterns corresponding to the plurality of diagnostic findings, and
change display positions of the plurality of diagnostic finding icons on the monitor in accordance with final similarities determined for the image patterns corresponding to the plurality of diagnostic findings.

2. The ultrasound diagnostic apparatus according to claim 1,
wherein the diagnostic apparatus body further includes an input device configured to accept an input operation by a user, and
the processor is further configured to link a diagnostic finding corresponding to a diagnostic finding icon selected through the input device among the plurality of diagnostic finding icons displayed on the monitor to the ultrasound diagnosis image.

3. The ultrasound diagnostic apparatus according to claim 2,
wherein the processor is further configured to display the diagnostic finding linked to the ultrasound diagnosis image on the monitor.

4. The ultrasound diagnostic apparatus according to claim 3,
wherein the processor is further configured to arrange the plurality of diagnostic finding icons corresponding to the plurality of diagnostic findings in a descending order of the similarity.

5. The ultrasound diagnostic apparatus according to claim 3,
wherein the ultrasound diagnosis image is an ultrasound image obtained by imaging a lung of a subject, and
at least one of the plurality of diagnostic findings includes a diagnostic finding of any of B-line, consolidation, normality, and absence of lung sliding.

6. The ultrasound diagnostic apparatus according to claim 2,
wherein the processor is further configured to arrange the plurality of diagnostic finding icons corresponding to the plurality of diagnostic findings in a descending order of the similarity.

7. The ultrasound diagnostic apparatus according to claim 2,
wherein the ultrasound diagnosis image is an ultrasound image obtained by imaging a lung of a subject, and at least one of the plurality of diagnostic findings includes a diagnostic finding of any of B-line, consolidation, normality, and absence of lung sliding.

8. The ultrasound diagnostic apparatus according to claim 1,
wherein the processor is further configured to arrange the plurality of diagnostic finding icons corresponding to the plurality of diagnostic findings in a descending order of the similarity.

9. The ultrasound diagnostic apparatus according to claim 8,
wherein the processor is further configured to display a diagnostic finding icon corresponding to a diagnostic finding of highest similarity among the plurality of diagnostic findings to be larger than the other diagnostic finding icons.

10. The ultrasound diagnostic apparatus according to claim 8,
wherein the ultrasound diagnosis image is an ultrasound image obtained by imaging a lung of a subject, and
at least one of the plurality of diagnostic findings includes a diagnostic finding of any of B-line, consolidation, normality, and absence of lung sliding.

11. The ultrasound diagnostic apparatus according to claim 1,
wherein the ultrasound diagnosis image is an ultrasound image obtained by imaging a lung of a subject, and
at least one of the plurality of diagnostic findings includes a diagnostic finding of any of B-line, consolidation, normality, and absence of lung sliding.

12. A control method of an ultrasound diagnostic apparatus, the control method comprising:
displaying an ultrasound diagnosis image at a time of freezing and a plurality of diagnostic finding icons corresponding to a plurality of determined diagnostic findings on a monitor;
determining similarity between ultrasound diagnosis images of a plurality of frames constituting a video image in a determined time until freezing and each of a plurality of image patterns corresponding to the plurality of diagnostic findings;
determining a maximum similarity among a plurality of similarities determined from the ultrasound diagnosis images of the plurality of frames as a final similarity, for each of the image patterns corresponding to the plurality of diagnostic findings; and
changing display positions of the plurality of diagnostic finding icons on the monitor in accordance with final similarities determined for the image patterns corresponding to the plurality of diagnostic findings.

* * * * *